US010603085B2

(12) United States Patent
Tsai et al.

(10) Patent No.: US 10,603,085 B2
(45) Date of Patent: Mar. 31, 2020

(54) GUIDING APPARATUS FOR MINIMALLY INVASIVE PEDICLE SCREWS INSERTION

(71) Applicants: Chang Gung Memorial Hospital, Linkou, Taoyuan (TW); Ming Chi University of Technology, New Taipei (TW)

(72) Inventors: Tsung-Ting Tsai, Taoyuan (TW); Chih-Chung Hu, New Taipei (TW)

(73) Assignees: CHANG GUNG MEMORIAL HOSPITAL, LINKOU, Taoyuan (TW); MING CHI UNIVERSITY OF TECHNOLOGY, New Taipei (TW)

( * ) Notice: Subject to any disclaimer, the term of this patent is extended or adjusted under 35 U.S.C. 154(b) by 219 days.

(21) Appl. No.: 15/886,005

(22) Filed: Feb. 1, 2018

(65) Prior Publication Data

US 2018/0296254 A1    Oct. 18, 2018

(30) Foreign Application Priority Data

Apr. 12, 2017    (TW) .............................. 106112108 A (51) Int. Cl.
| | | |
|---|---|---|
| *A61B 17/70* | (2006.01) | |
| *A61B 17/88* | (2006.01) | |
| *A61B 17/17* | (2006.01) | |
| *A61B 90/00* | (2016.01) | |

(Continued)

(52) U.S. Cl.
CPC ...... *A61B 17/7076* (2013.01); *A61B 17/1757* (2013.01); *A61B 17/7032* (2013.01); *A61B 17/8897* (2013.01); *A61B 2017/00238* (2013.01); *A61B 2017/90* (2013.01); *A61B 2090/3762* (2016.02)

(58) Field of Classification Search
CPC ........................ A61B 17/7076; A61B 17/1757
See application file for complete search history.

(56) References Cited

U.S. PATENT DOCUMENTS 9,198,678 B2 † 12/2015 Frey
2001/0049527 A1* 12/2001 Cragg ................ A61B 17/1671
606/279

(Continued)

FOREIGN PATENT DOCUMENTS

CN            2776329 Y      5/2006

*Primary Examiner* — Christian A Sevilla
(74) *Attorney, Agent, or Firm* — Guice Patents PLLC (57) ABSTRACT

A guiding apparatus for pedicle screws insertion, including: two orientation rods, used to be fixed on a bone to provide two non-parallel rod bodies; an orientation board, having a first orientation tube, a second orientation tube, a lengthy lateral opening, and a plurality of sleeve combinations, the second orientation tube having a vertical opening connected with the lengthy lateral opening, so that when one rod body of the two non-parallel rod bodies passes through the first orientation tube, the other rod body of the two non-parallel rod bodies will move through the lengthy lateral opening and enter the second orientation tube via the vertical opening; and a plurality of metal pins, used to be inserted into the bone through the plurality of sleeve combinations, and guide a plurality of pedicle screws to be screwed into the bone after inner sleeves of the sleeve combinations are removed.

10 Claims, 13 Drawing Sheets

(51) Int. Cl.
 *A61B 17/90* (2006.01)
 *A61B 17/00* (2006.01)

(56) References Cited

U.S. PATENT DOCUMENTS

| | | | | |
|---|---|---|---|---|
| 2007/0167946 A1* | 7/2007 | Triplett | .............. | A61B 17/1757 606/279 |
| 2010/0152790 A1* | 6/2010 | Hestad | ............... | A61B 17/7083 606/86 A |
| 2011/0009969 A1* | 1/2011 | Puno | ................... | A61B 17/1757 623/17.12 |
| 2016/0296259 A1* | 10/2016 | Lee | ..................... | A61B 17/7071 |
| 2017/0311961 A1* | 11/2017 | Lipari | ................. | A61B 17/1757 |

\* cited by examiner
† cited by third party

GUIDING APPARATUS FOR MINIMALLY INVASIVE PEDICLE SCREWS INSERTION

BACKGROUND OF THE INVENTION

Field of the Invention

The present invention relates to a guiding apparatus for minimally invasive pedicle screws insertion, especially to a guiding apparatus capable of allowing plural pedicle screws to be accurately screwed into a bone of a spine in a minimally invasive way.

Description of the Related Art

Pedicle fixation surgery is mainly adopted for curing degenerative spinal disease, spinal canal stenosis, vertebral fracture or vertebral deformity, etc. In conventional orthopedic surgery, the pedicle screws insertion relies heavily on a surgeon's experiences to determine insertion positions and angles. However, a surgeon is likely to insert the pedicle screws into a bone of a spine at deviated positions or with improper orientations, and this can cause the pedicle screws to deviate out of the bone to hurt vessels and nervous tissues around the spine, and even result in serious complications. Besides, repeatedly adjusting the insertion positions and angles will not only prolong surgery time, but can even damage the bone tissues, and the fixation effect can be thereby compromised. In addition, as an X-ray photograph has to be taken during the pedicle screws insertion surgery, the patient and the medical crews will be subjected to a risk of radiation exposure. To prevent the risk, a hospital has to spend a lot of money to purchase a navigation system and intraoperative imaging equipment.

To solve the problems that can happen in the pedicle screws insertion surgery performed purely based on a surgeon's experiences, some guiding apparatuses for pedicle screws insertion have been proposed. For example, the China patent CN2776329Y discloses a "pedicle screws fixator" having a technical scheme that an extendable transverse rod is hinged between two sleeve pipes through a fixing module to form an H-shaped support frame; a small sleeve pipe is installed in the vertical direction at the middle part of the transverse rod, and a fixing needle is installed inside the small sleeve pipe; and two tapping cones are installed inside the two sleeve pipes respectively. The transverse rod has metric scales along its length, and the tapping cones and the fixing needle all have metric scales along a length upward form a tip. However, the technical scheme still cannot avoid the problems of deviated positions or improper orientations of pedicle screws insertion caused by human judgement.

To solve the problems of deviated positions or improper orientations of pedicle screws insertion caused by unreliable human judgement, and exclude the need of using an expensive navigation systems and expensive intraoperative imaging equipment, a novel guiding apparatus for minimally invasive pedicle screws insertion is needed.

SUMMARY OF THE INVENTION

One objective of the present invention is to disclose a guiding apparatus for minimally invasive pedicle screws insertion, which is capable of providing a high accuracy guiding operation and thereby resulting in an excellent fixation effect.

Another objective of the present invention is to disclose a guiding apparatus for minimally invasive pedicle screws insertion, which is capable of providing a high accuracy guiding mechanism to allow a minimally invasive surgery to reduce operative incisions and prevent hurting vessels and nervous tissues around the spine.

Still another objective of the present invention is to disclose a guiding apparatus for minimally invasive pedicle screws insertion, which is capable of providing accurate insertion paths of pedicle screws for a surgeon so that the surgeon can perform the surgery without the need of adjusting the insertion positions and angles of the pedicle screws, thereby shortening the surgery time.

To attain the foregoing objectives, a guiding apparatus for minimally invasive pedicle screws insertion is proposed, including:

two orientation rods, each having a fixing end for fixing on a bone of a spine of a patient to provide two non-parallel rod bodies;

an orientation board, having a board body, a first orientation tube and a second orientation tube installed inside two orientation holes of the board body respectively, and a plurality of sleeve combinations installed inside a plurality of guiding holes of the board body, wherein, each of the sleeve combinations has an inner sleeve and an outer sleeve, the board body has a lengthy lateral opening, and the second orientation tube has a vertical opening connected with the lengthy lateral opening, so that when one rod body of the two non-parallel rod bodies passes through the first orientation tube, the other rod body of the two non-parallel rod bodies will move through the lengthy lateral opening and enter the second orientation tube via the vertical opening, thereby completing an orientation process; and a plurality of metal pins, used to be inserted into the bone of the spine through the plurality of sleeve combinations after the orientation process is completed, and used to guide a plurality of pedicle screws to be screwed into the bone of the spine after the inner sleeves of the sleeve combinations are removed.

In one embodiment, the fixing end includes a socket and a screw, wherein the screw is used to be screwed into the bone of the spine, and the socket is used to connect with the screw.

In one embodiment, the guiding apparatus for minimally invasive pedicle screws insertion further includes two clamping units, one of which being used for clamping together one of the two orientation rods and the first orientation tube, and the other of which being used for clamping together the other of the two orientation rods and the second orientation tube after the orientation process is completed.

In one embodiment, the metal pins are made of steel or titanium alloy.

In one embodiment, the board body has a curved surface and the plurality of guiding holes are determined according to an X-ray computed tomography image, which contains an image of the bone of the spine and an image of the two orientation rods fixed on the bone of the spine.

To attain the foregoing objectives, another guiding apparatus for minimally invasive pedicle screws insertion is proposed, including:

an orientation rod, having a fixing end and a rod body, the fixing end being used for fixing on a bone of a spine of a patient to make the rod body extending outside the bone of the spine;

an orientation board, having a board body, an orientation unit installed inside an orientation hole of the board body, and a plurality of sleeve combinations installed inside a plurality of guiding holes of the board body, wherein, the orientation unit includes a tube and an orientation socket connected with the tube, and each of the sleeve combinations has an inner sleeve and an outer sleeve, so that after the orientation rod is fixed on the bone of the spine, the tube and the orientation socket of the orientation unit will pass through the rod body and the orientation socket will socket a local area of the bone of the spine, thereby completing an orientation process; and a plurality of metal pins, used to be inserted into the bone of the spine through the plurality of sleeve combinations after the orientation process is completed, and used to guide a plurality of pedicle screws to be screwed into the bone of the spine after the inner sleeves of the sleeve combinations are removed.

In one embodiment, the fixing end includes a socket and a screw, wherein the screw is used to be screwed into the bone of the spine, and the socket is used to connect with the screw.

In one embodiment, the guiding apparatus for minimally invasive pedicle screws insertion further includes a clamping unit for clamping together the orientation rod and the orientation unit after the orientation process is completed.

In one embodiment, the metal pins are made of steel or titanium alloy.

In one embodiment, the board body has a curved surface and the plurality of guiding holes are determined according to an X-ray computed tomography image, which contains an image of the bone of the spine and an image of the orientation rod fixed on the bone of the spine.

To make it easier for our examiner to understand the objective of the invention, its structure, innovative features, and performance, we use preferred embodiments together with the accompanying drawings for the detailed description of the invention.

DETAILED DESCRIPTION OF THE PREFERRED EMBODIMENTS

Figure 1:
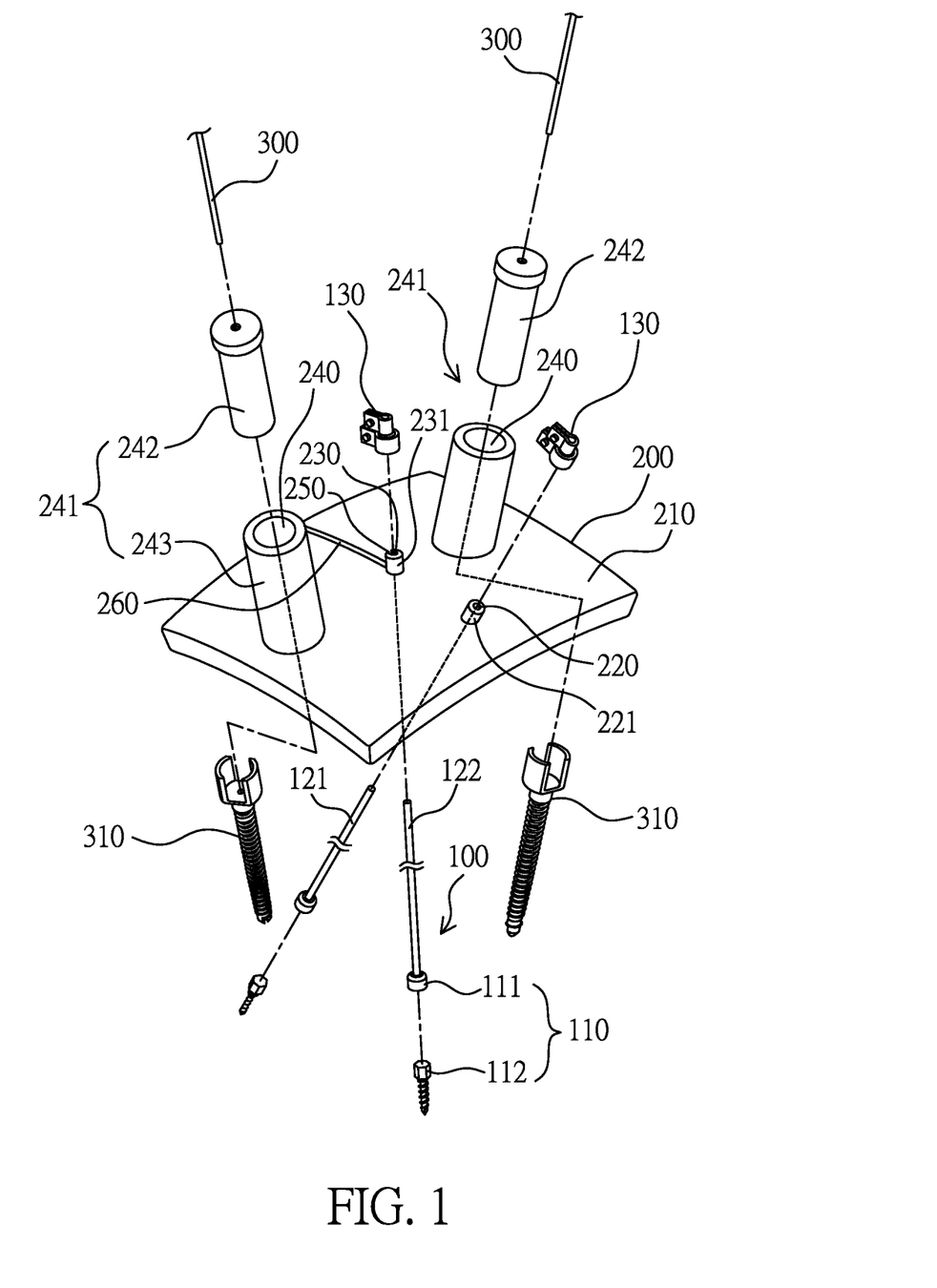
FIG. 1 illustrates an exploded view of a guiding apparatus for minimally invasive pedicle screws insertion of the present invention according to a preferred embodiment of the present invention.

Please refer to FIG. 1, which illustrates an exploded view of a guiding apparatus for minimally invasive pedicle screws insertion of the present invention according to a preferred embodiment of the present invention.

As illustrated in FIG. 1, the guiding apparatus for minimally invasive pedicle screws insertion includes two orientation rods 100, an orientation board 200, and a plurality of metal pins 300. In this embodiment, two metal pins 300 are used.

The two orientation rods 100, each of which has a fixing end 110 for fixing on a bone of a spine of a patient to provide two non-parallel rod bodies 121, 122, the fixing end 110 includes a socket 111 and a screw 112, wherein the socket 111 is used to connect with the screw 112, and the screw 112 is used to be screwed into the bone of the spine.

The orientation board 200 has a board body 210, which can be a plain board body or a curved-surface board body, and the board body 210 includes a first orientation hole 220 and a first orientation tube 221 installed inside the first orientation hole 220, a second orientation hole 230 and a second orientation tube 231 installed inside the second orientation hole 230, a plurality of guiding holes 240 and a plurality of sleeve combinations 241 installed inside the plurality of guiding holes 240, and each of the sleeve combinations 241 has an inner sleeve 242 and an outer sleeve 243. In this embodiment, two guiding holes 240 and two sleeve combinations 241 are used.

Figure 2:
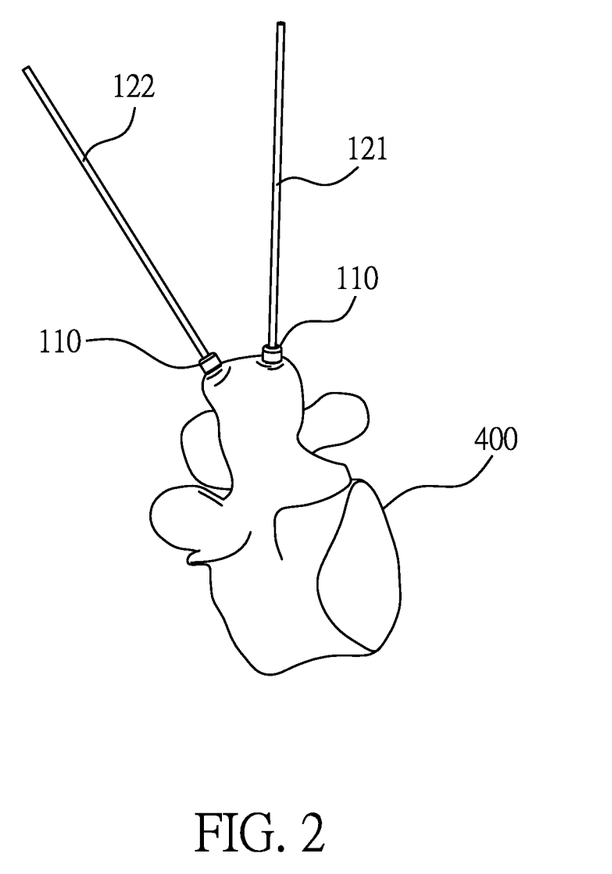
FIG. 2 illustrates a situation that two non-parallel rods of the guiding apparatus for minimally invasive pedicle screws insertion of FIG. 1 are screwed into a bone of a spine.

Please refer to FIG. 2, which illustrates a situation that two non-parallel rods of the guiding apparatus for minimally invasive pedicle screws insertion of FIG. 1 are screwed into a bone of a spine.

As illustrated in FIG. 2, each of the two orientation rods 100 has a fixing end 110 fixed on a bone 400 of a spine of a patient to provide two non-parallel rod bodies 121, 122.

Besides, by performing an X-ray computed tomography scan on the bone 400 of the spine and the two non-parallel rod bodies 121, 122 extending from the bone 400 of the spine, a stereo image can be derived and used for determining the positions and orientations of the first orientation hole 220, the second orientation hole 230, and the plurality of guiding holes 240 on the orientation board 200.

Figure 3A:
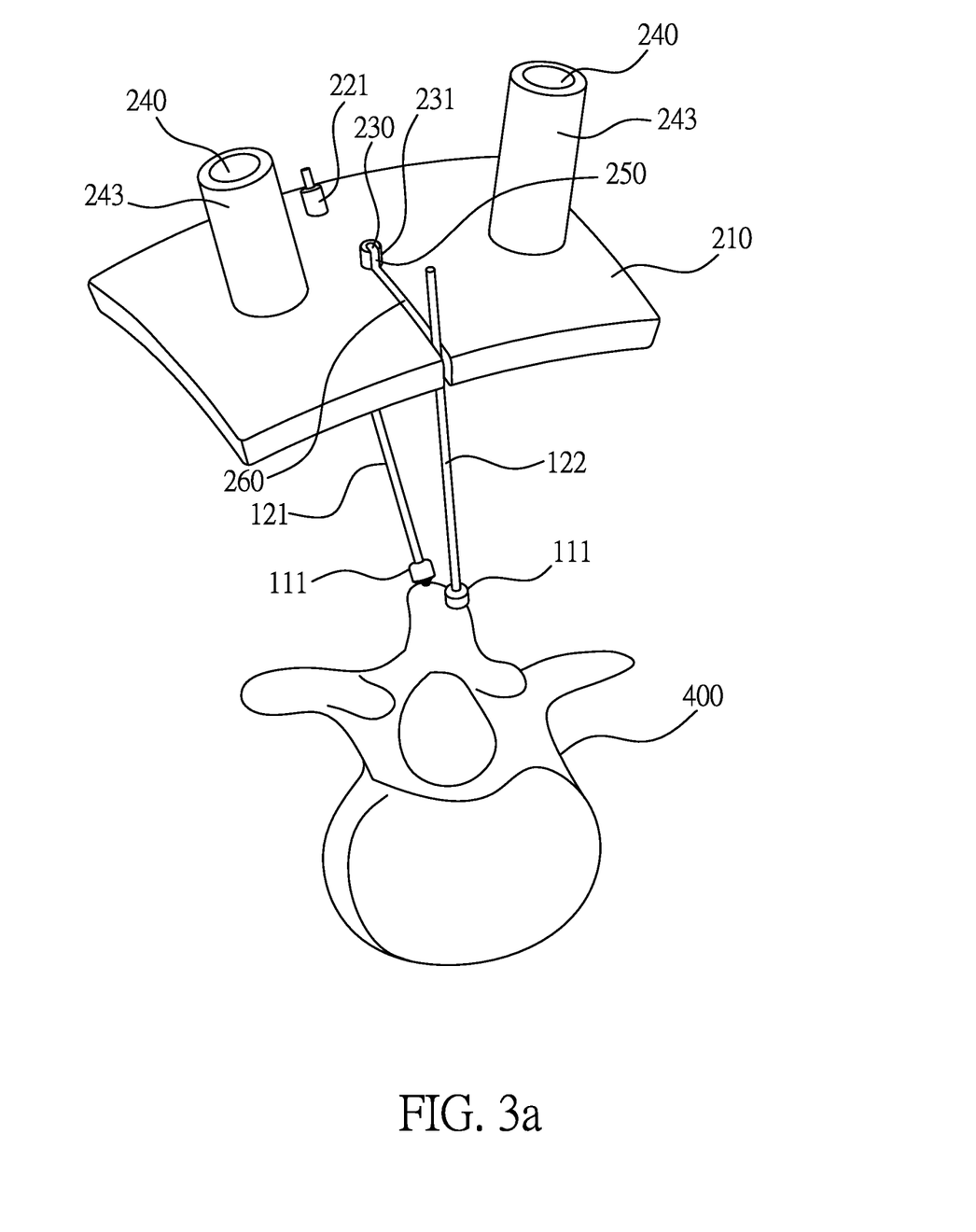
FIG. 3a-3c illustrate an orientation process of the guiding apparatus for minimally invasive pedicle screws insertion of FIG. 1, in which a second rod gradually moves along a lengthy lateral opening of an orientation board to enter a second orientation tube.
Figure 3B:
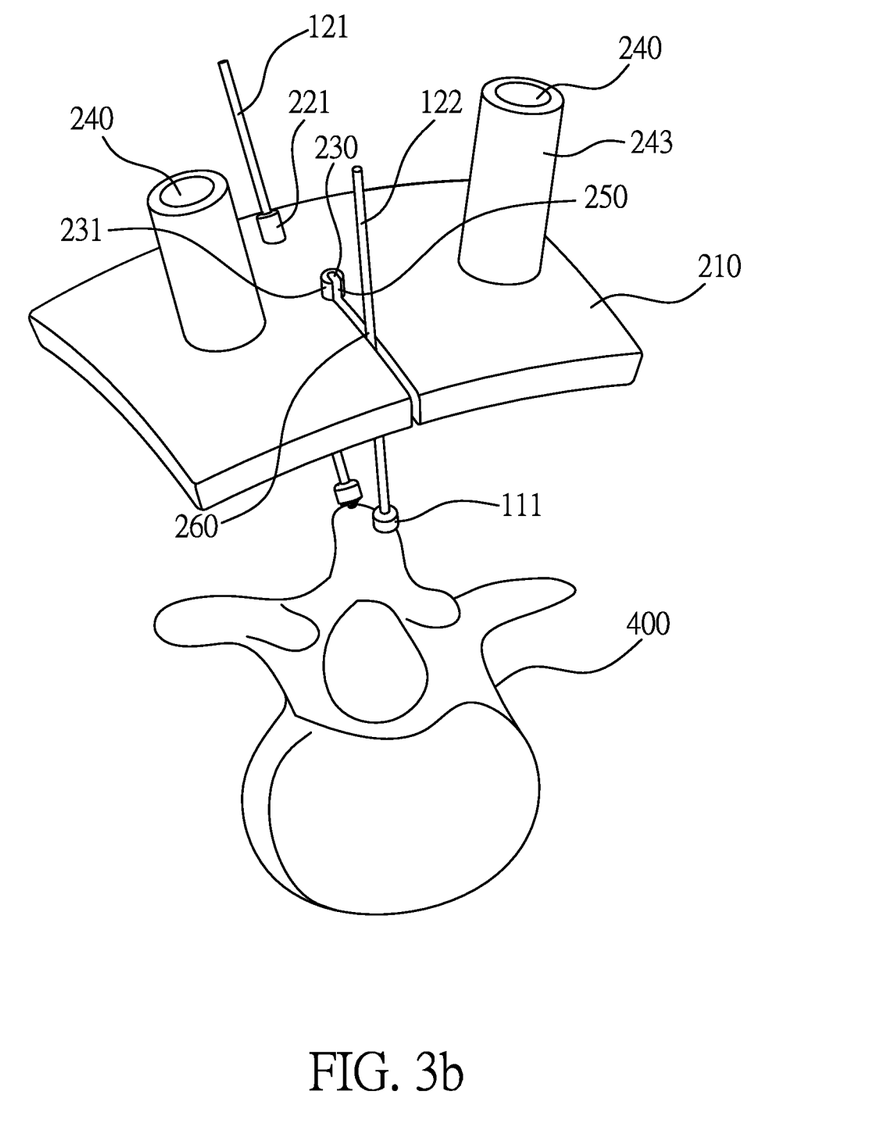
Figure 3C:
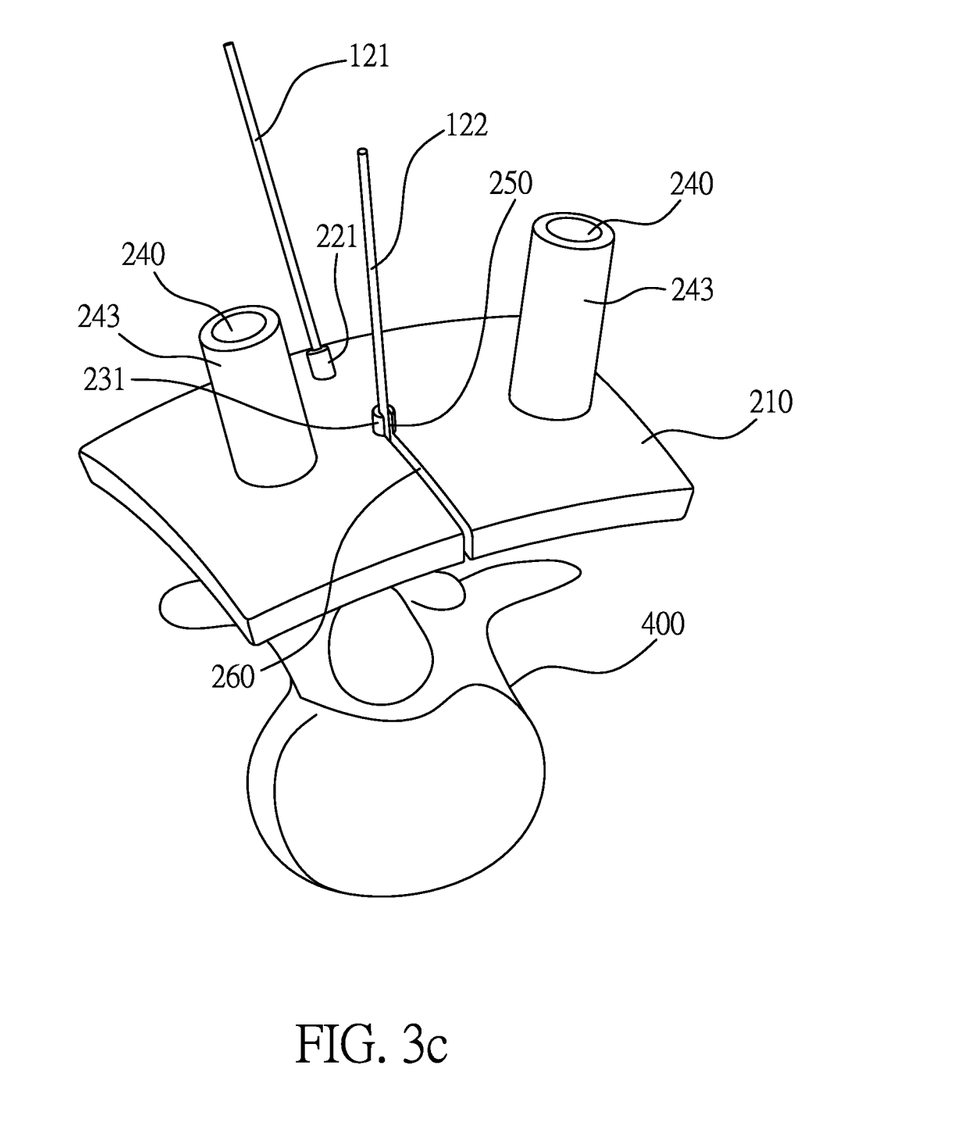

Please refer to FIG. 3a-3c, which illustrate an orientation process of the guiding apparatus for minimally invasive pedicle screws insertion of FIG. 1, wherein, the rod body 122 gradually moves along a lengthy lateral opening 260 of the orientation board 200 to enter the second orientation tube 231.

As illustrated in FIG. 3a, when the board body 210 is at an initial position away from the bone 400 of the spine, the rod body 122 is located at an entrance of the lengthy lateral opening 260.

As illustrated in FIG. 3b, as the board body 210 approaches the bone 400 of the spine, the rod body 122 moves along the lengthy lateral opening 260 to approach a vertical opening 250 of the second orientation tube 231, the vertical opening 250 being connected with the lengthy lateral opening 260.

As illustrated in FIG. 3c, an orientation process is completed when the board body 210 reaches a position near the bone 400 of the spine to make the rod body 122 enter the second orientation tube 231 via the vertical opening 250.

Figure 4:
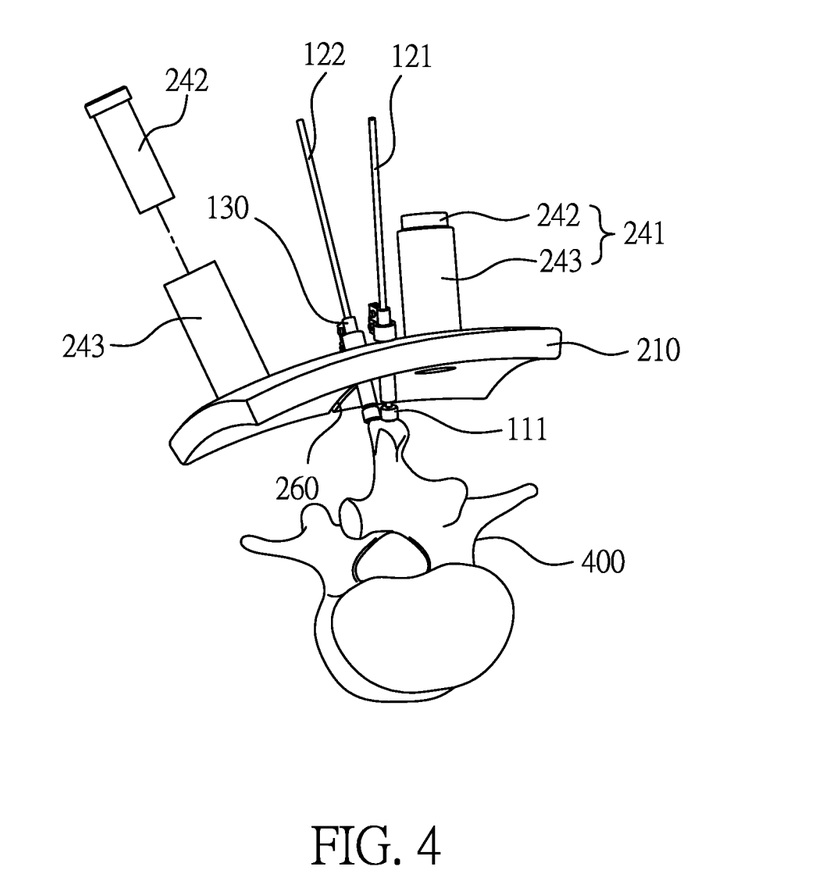
FIG. 4 illustrates a scenario that an inner tube of the guiding apparatus for minimally invasive pedicle screws insertion of FIG. 1 is to be installed into an outer tube.
Figure 5:
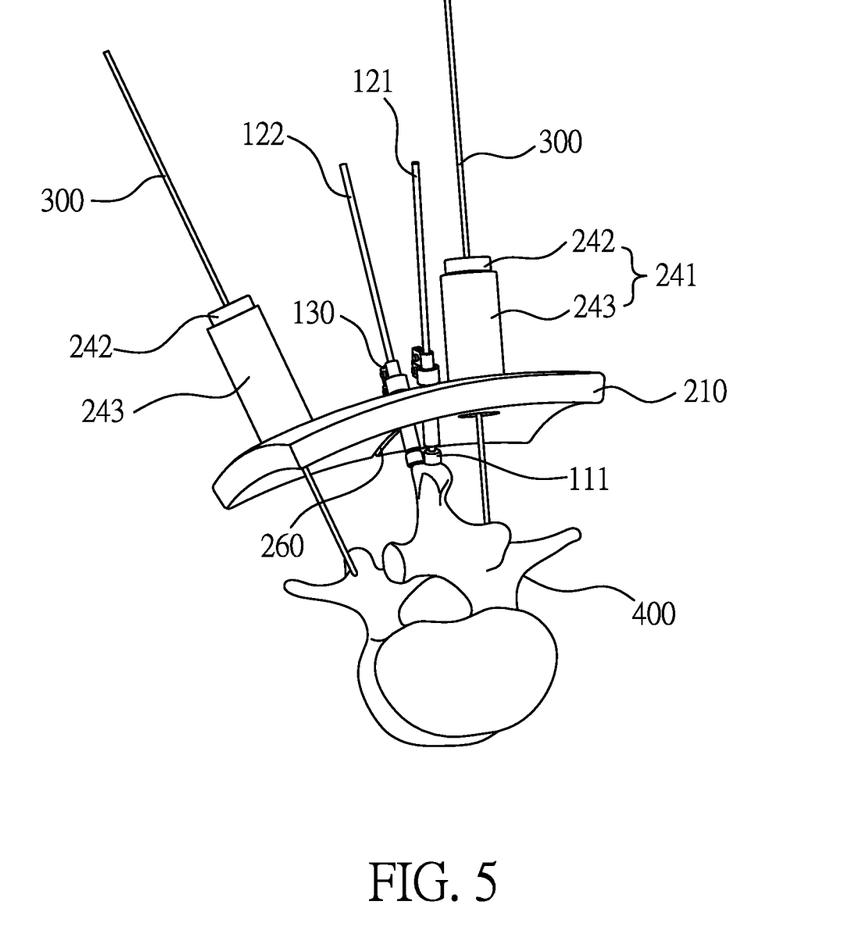
FIG. 5 illustrates a situation that two metal pins of the guiding apparatus for minimally invasive pedicle screws insertion of FIG. 1 are guided by two tube combinations to penetrate into a bone of a spine.
Figure 6:
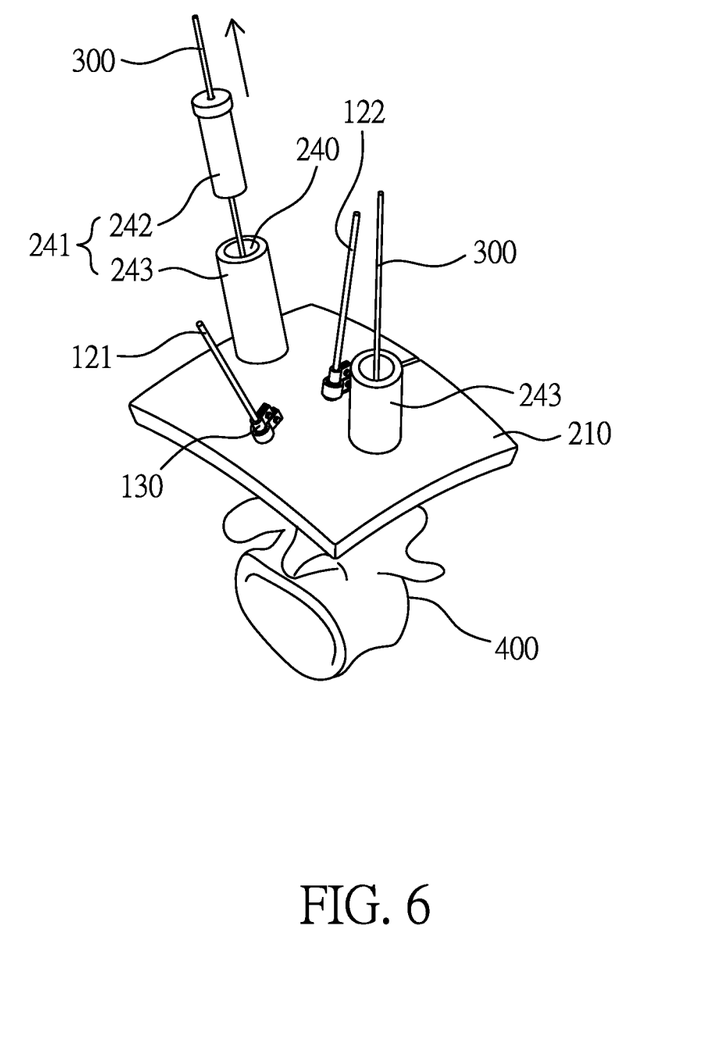
FIG. 6 illustrates a scenario that one inner tube is removed and the other inner tube is to be removed after an orientation process of the guiding apparatus for minimally invasive pedicle screws insertion of FIG. 1 is completed.

Please refer to FIG. 4-6, wherein FIG. 4 illustrates a scenario that an inner tube of the guiding apparatus for minimally invasive pedicle screws insertion of FIG. 1 is to be installed into an outer tube; FIG. 5 illustrates a situation that two metal pins of the guiding apparatus for minimally invasive pedicle screws insertion of FIG. 1 are guided by two tube combinations to penetrate into a bone of a spine; and FIG. 6 illustrates a scenario that one inner tube is removed and the other inner tube is to be removed after an orientation process of the guiding apparatus for minimally invasive pedicle screws insertion of FIG. 1 is completed.

As illustrated in FIG. 4, the two orientation rods 100 further includes two clamping units 130, one of which being used for clamping together one of the two orientation rods 100 and the first orientation tube 221, and the other of which being used for clamping together the other of the two orientation rods 100 and the second orientation tube 231 after the orientation process is completed. After that, as illustrated in FIG. 5, two inner sleeves 242 are installed into two outer sleeves 243 to form two sleeve combinations 241, and two metal pins 300 are guided by the two sleeve combinations 241 respectively to penetrate into the bone 400 of the spine, wherein the metal pins 300 are preferably made of a metal material having proper hardness, such as steel or titanium alloy, etc. After the two metal pins 300 are inserted into the bone 400 of the spine, as illustrated in FIG. 6, the inner sleeves 242 of the sleeve combinations 241 are removed to enable the sleeve combinations 241 to guide two pedicle screws 310 to be screwed into the bone 400 of the spine.

Figure 7:
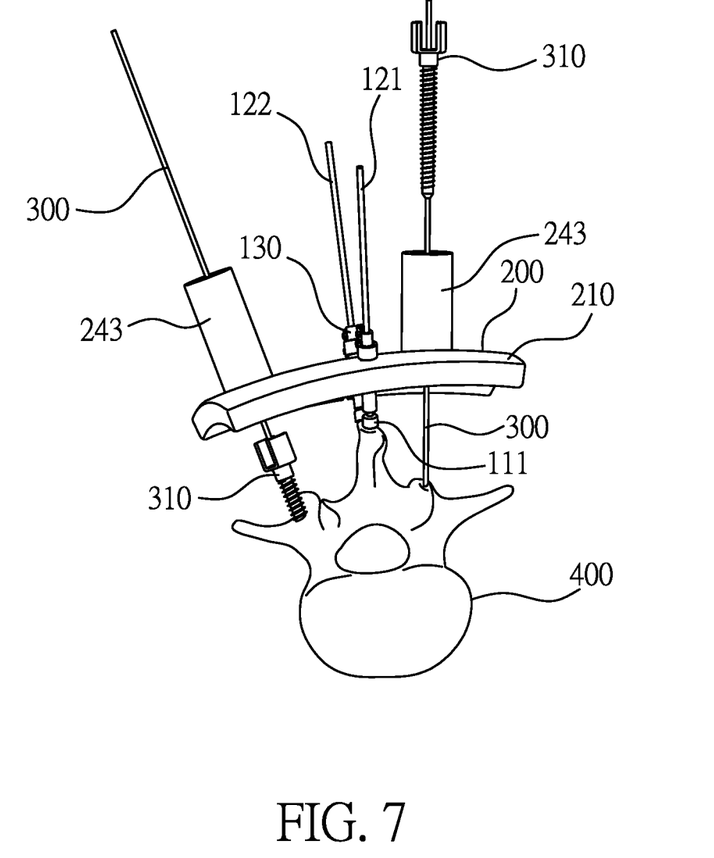
FIG. 7-8 illustrate a screw-insertion process of the guiding apparatus for minimally invasive pedicle screws insertion of FIG. 1, in which two pedicle screws are guided by two metal pins respectively to be screwed into a bone of a spine.
Figure 8:
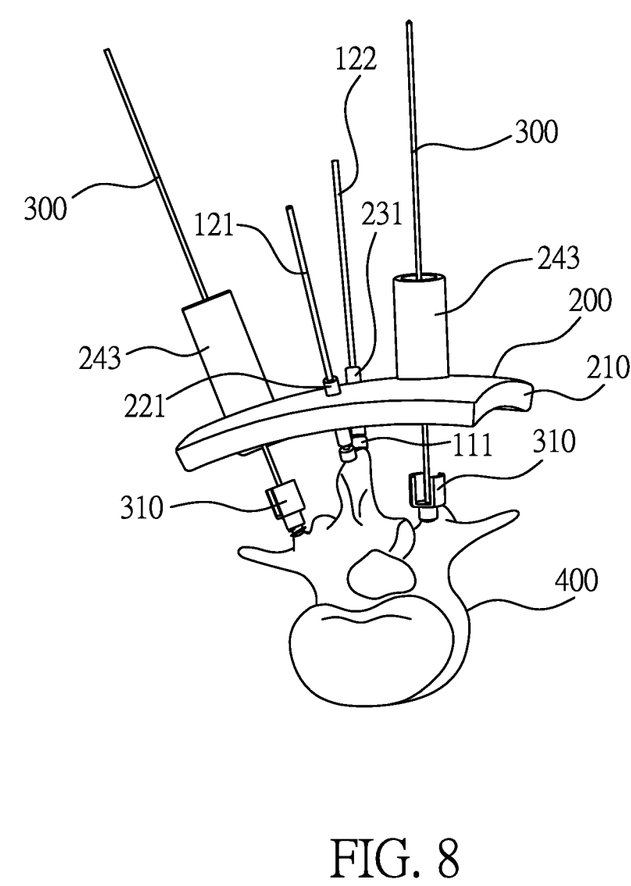
Figure 9:
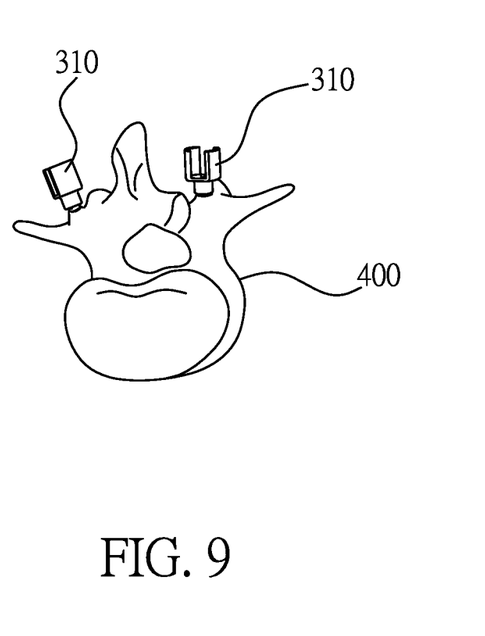
FIG. 9 illustrates an outline of a bone of a spine fixed with two pedicle screws after the operation of the guiding apparatus for minimally invasive pedicle screws insertion of FIG. 1 is completed.

Please refer to FIG. 7-8, which illustrate a screw-insertion process of the guiding apparatus for minimally invasive pedicle screws insertion of FIG. 1, in which two pedicle screws 310 are guided by two metal pins 300 respectively to be screwed into the bone 400 of the spine. After the two pedicle screws 310 are screwed into the bone 400 of the spine, all the two orientation rods 100, the orientation board 200, and the two metal pins 300 are removed, and the bone 400 of the spine is fixed with two pedicle screws 310 as illustrated in FIG. 9.

Figure 10:
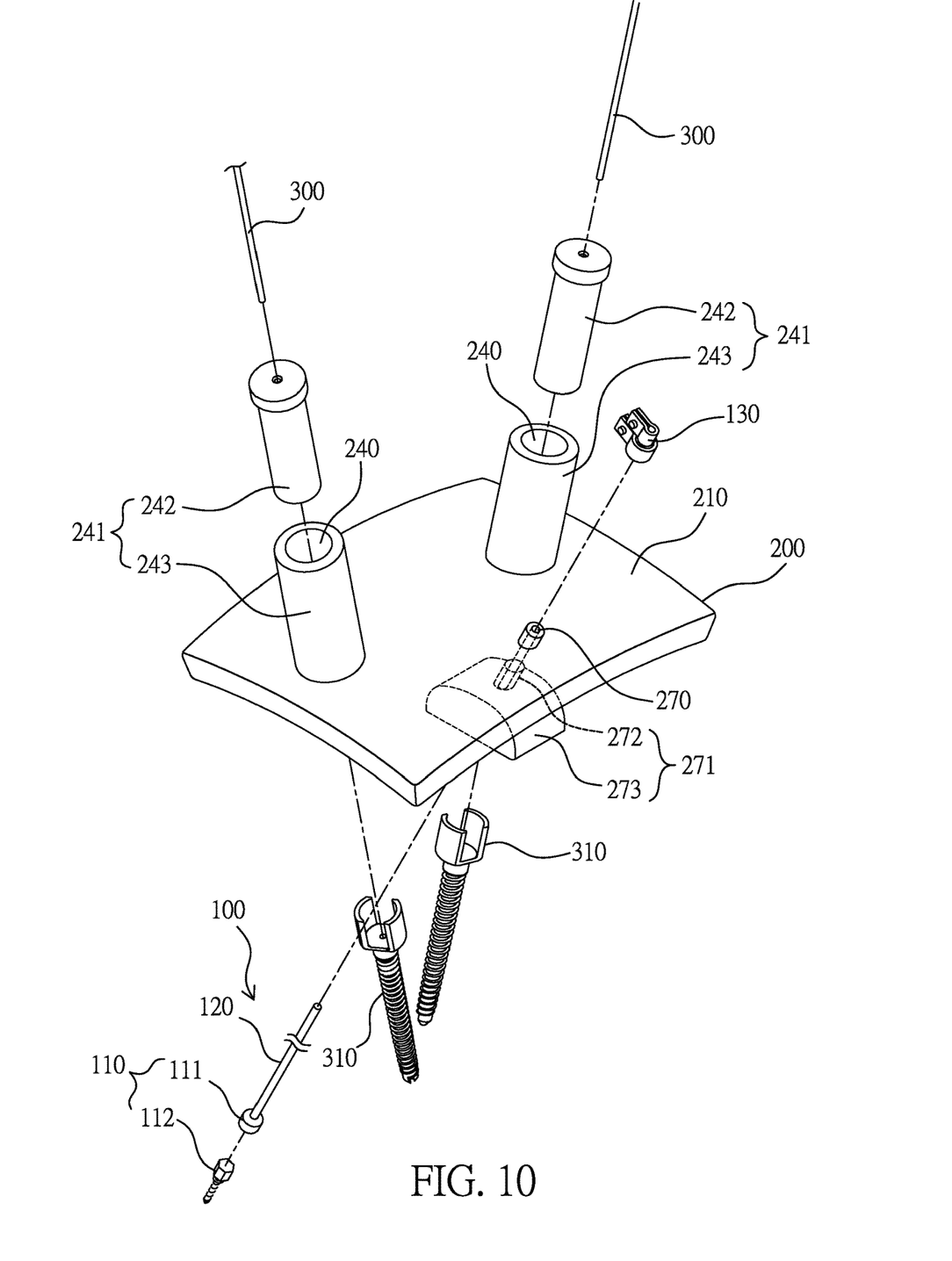
FIG. 10 illustrates an exploded view of a guiding apparatus for minimally invasive pedicle screws insertion of the present invention according to another preferred embodiment of the present invention.

Please refer to FIG. 10, which illustrates an exploded view of a guiding apparatus for minimally invasive pedicle screws insertion of the present invention according to another preferred embodiment of the present invention.

As illustrated in FIG. 10, the guiding apparatus for minimally invasive pedicle screws insertion includes an orientation rod 100, an orientation board 200, and a plurality of metal pins 300. In this embodiment, two metal pins 300 are used.

The orientation rod 100 has a fixing end 110 and a rod body 120, the fixing end 110 being used for fixing on a bone 400 of a spine of a patient to make the rod body 120 extending outward from the bone 400 of the spine. The fixing end 110 includes a socket 111 and a screw 112, wherein the socket 111 is used to connect with the screw 112, and the screw 112 is used to be screwed into the bone 400 of the spine.

The orientation board 200 has a board body 210, an orientation unit 271 installed inside an orientation hole 270 of the board body 210, and a plurality of sleeve combinations 241 installed inside a plurality of guiding holes 240 of the board body 210, wherein each of the sleeve combinations 241 has an inner sleeve 242 and an outer sleeve 243. In this embodiment, two guiding holes 240 and two sleeve combinations 241 are used.

The orientation unit 271 includes a tube 272 and an orientation socket 273 connected with the tube 272, so that after the orientation rod 100 is fixed on the bone 400 of the spine (not shown in this figure), the tube 272 and the orientation socket 273 of the orientation unit 271 will pass through the rod body 120 and the orientation socket 273 will socket a local area of the bone 400 of the spine, thereby completing an orientation process.

Besides, the orientation rod 100 can further include a clamping unit 130 for clamping together the orientation rod 100 and the orientation unit 271 after the orientation process is completed.

The board body 210 can be a plain board body or a curved-surface board body, and the plurality of guiding holes 240 are determined according to an X-ray computed tomography image (not shown in the figure), which contains an image of the bone 400 of the spine and an image of the orientation rod 100 fixed on the bone 400 of the spine.

Figure 11:
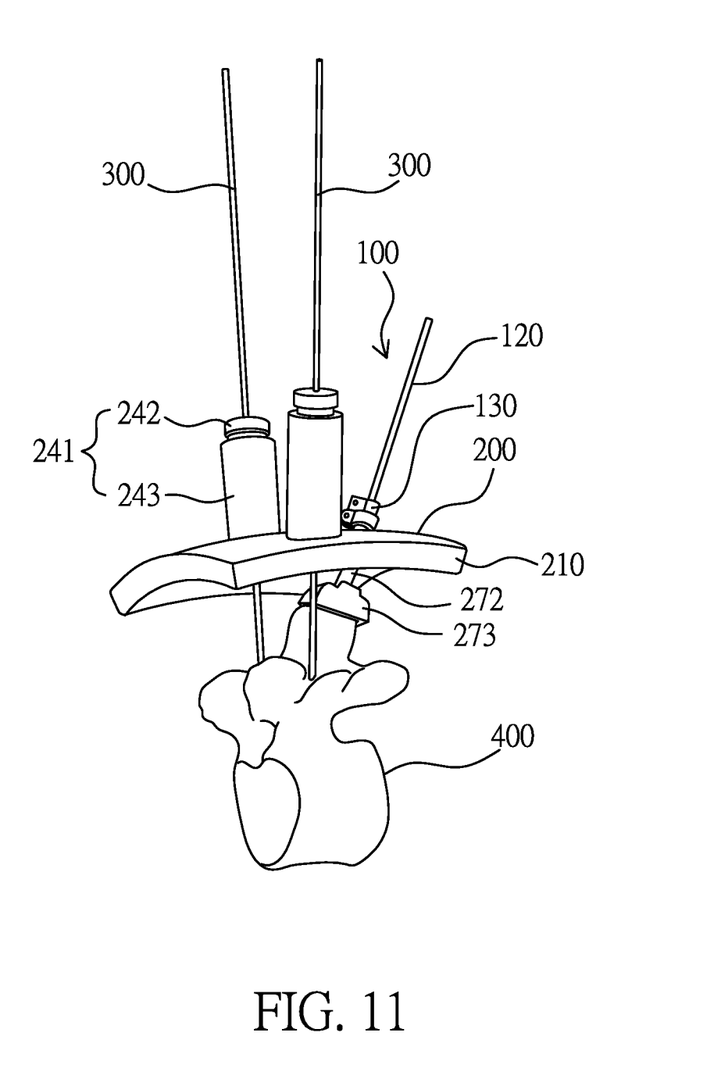
FIG. 11 illustrates a situation that two metal pins of the guiding apparatus for minimally invasive pedicle screws insertion of FIG. 10 are guided by two tube combinations to penetrate into a bone of a spine.

FIG. 11 illustrates a situation that two metal pins of the guiding apparatus for minimally invasive pedicle screws insertion of FIG. 10 are guided by two tube combinations to penetrate into a bone of a spine. As illustrated in FIG. 11, two metal pins 300 are guided by two tube combinations 241 to penetrate into the bone of the spine after the orientation process is completed, and the two metal pins 300 are preferably made of a metal material having proper hardness, such as steel or titanium alloy, etc. After the inner sleeves 242 of the sleeve combinations 241 are removed, the two pedicle screws 310 can thereby be guided to be screwed into the bone 400 of the spine, and after the two pedicle screws 310 are screwed into the bone 400 of the spine, all the two orientation rods 100, the orientation board 200, and the two metal pins 300 will be removed to complete a pedicle fixation surgery.

Thanks to the designs disclosed above, the present invention possesses the advantages as follows:

1. The guiding apparatus for minimally invasive pedicle screws insertion of the present invention can provide a high accuracy guiding operation and thereby result in an excellent fixation effect.

2. The guiding apparatus for minimally invasive pedicle screws insertion of the present invention can provide a high accuracy guiding mechanism to allow a minimally invasive surgery to reduce operative incisions and prevent hurting vessels and nervous tissues around the spine.

3. The guiding apparatus for minimally invasive pedicle screws insertion of the present invention can provide accurate insertion paths of pedicle screws for a surgeon so that the surgeon can perform the surgery without the need of adjusting the insertion positions and angles of the pedicle screws, thereby shortening the surgery time.

While the invention has been described by way of example and in terms of preferred embodiments, it is to be understood that the invention is not limited thereto. On the contrary, it is intended to cover various modifications and similar arrangements and procedures, and the scope of the appended claims therefore should be accorded the broadest interpretation so as to encompass all such modifications and similar arrangements and procedures.

In summation of the above description, the present invention herein enhances the performance over the conventional structure and further complies with the patent application requirements and is submitted to the Patent and Trademark Office for review and granting of the commensurate patent rights.

What is claimed is:

1. A guiding apparatus for minimally invasive pedicle screws insertion, including:

two orientation rods, each having a fixing end for fixing on a bone of a spine of a patient to provide two non-parallel rod bodies;

an orientation board, having a board body, a first orientation tube and a second orientation tube installed inside two orientation holes of the board body respectively, and a plurality of sleeve combinations installed on the board body, wherein, each of the sleeve combinations has an inner sleeve and an outer sleeve, each said inner sleeve is inserted into a corresponding guiding hole, the board body has a lengthy lateral opening, and the second orientation tube has a vertical opening connected with the lengthy lateral opening, so that when one rod body of the two non-parallel rod bodies passes through the first orientation tube, the other rod body of the two non-parallel rod bodies will move through the lengthy lateral opening and enter the second orientation tube via the vertical opening, thereby completing an orientation process; and a plurality of metal pins, used to be inserted into the bone of the spine through the plurality of sleeve combinations after the orientation process is completed, and used to guide a plurality of pedicle screws to be screwed into the bone of the spine after the inner sleeves of the sleeve combinations are removed.

2. The guiding apparatus for minimally invasive pedicle screws insertion as disclosed in claim 1, wherein each said fixing end includes a socket and a screw, the screw being used to be screwed into the bone of the spine, and the socket being used to connect with the screw.

3. The guiding apparatus for minimally invasive pedicle screws insertion as disclosed in claim 1, wherein the guiding apparatus for minimally invasive pedicle screws insertion further includes two clamping units, one of which being used for clamping together one of the two orientation rods and the first orientation tube, and the other of which being used for clamping together the other of the two orientation rods and the second orientation tube after the orientation process is completed.

4. The guiding apparatus for minimally invasive pedicle screws insertion as disclosed in claim 1, wherein the metal pins are made of steel or titanium alloy.

5. The guiding apparatus for minimally invasive pedicle screws insertion as disclosed in claim 1, wherein the board body has a curved surface and the plurality of guiding holes are determined according to an X-ray computed tomography image, which contains an image of the bone of the spine and an image of the two orientation rods fixed on the bone of the spine.

6. A guiding apparatus for minimally invasive pedicle screws insertion, including:

an orientation rod, having a fixing end and a rod body, the fixing end being used for fixing on a bone of a spine of a patient to make the rod body extending outside the bone of the spine;

an orientation board, having a board body, an orientation unit installed inside an orientation hole of the board body, and a plurality of sleeve combinations installed on the board body, wherein, the orientation unit includes a tube and an orientation socket connected with the tube, and each of the sleeve combinations has an inner sleeve and an outer sleeve, each said inner sleeve is inserted into a corresponding guiding hole, so that after the orientation rod is fixed on the bone of the spine, the tube and the orientation socket of the orientation unit will pass through the rod body and the orientation socket will socket a local area of the bone of the spine, thereby completing an orientation process; and a plurality of metal pins, used to be inserted into the bone of the spine through the plurality of sleeve combinations after the orientation process is completed, and used to guide a plurality of pedicle screws to be screwed into the bone of the spine after the inner sleeves of the sleeve combinations are removed.

7. The guiding apparatus for minimally invasive pedicle screws insertion as disclosed in claim 6, wherein each said fixing end includes a socket and a screw, the screw being used to be screwed into the bone of the spine, and the socket being used to connect with the screw.

8. The guiding apparatus for minimally invasive pedicle screws insertion as disclosed in claim 6, further including a clamping unit for clamping together the orientation rod and the orientation unit after the orientation process is completed.

9. The guiding apparatus for minimally invasive pedicle screws insertion as disclosed in claim 6, wherein the metal pins are made of steel or titanium alloy.

10. The guiding apparatus for minimally invasive pedicle screws insertion as disclosed in claim 6, wherein the board body has a curved surface and the plurality of guiding holes are determined according to an X-ray computed tomography image, which contains an image of the bone of the spine and an image of the orientation rod fixed on the bone of the spine.

* * * * *